US00PP21451P3

(12) United States Plant Patent
Jackson et al.

(10) Patent No.: US PP21,451 P3
(45) Date of Patent: Nov. 9, 2010

(54) EASTERN REDBUD TREE NAMED 'JN2'

(50) Latin Name: *Cercis canadensis*
Varietal Denomination: JN2

(76) Inventors: Ray Jackson, 6115 Lexie Beans Creek Rd., Belvidere, TN (US) 37306; Cindy Jackson, 6115 Lexie Beans Creek Rd., Belvidere, TN (US) 37306

( * ) Notice: Subject to any disclaimer, the term of this patent is extended or adjusted under 35 U.S.C. 154(b) by 0 days.

(21) Appl. No.: 12/287,327

(22) Filed: Oct. 8, 2008

(65) Prior Publication Data

US 2010/0088792 P1 Apr. 8, 2010

(51) Int. Cl.
*A01H 5/00* (2006.01)

(52) U.S. Cl. ..... Plt./216
(58) Field of Classification Search ..... Plt./216
See application file for complete search history.

(56) References Cited

U.S. PATENT DOCUMENTS

PP17,740 P3 5/2007 Roethling

*Primary Examiner*—Susan B McCormick Ewoldt
(74) *Attorney, Agent, or Firm*—Polster, Lieder, Woodruff & Lucchesi, L.C.

(57) ABSTRACT

An Eastern Redbud tree named 'JN2' having golden orange new growth that does not burn, speckled lime green mature foliage, an improved vigor in heat and drought, and the capability of being reproduced reliably from budding.

7 Drawing Sheets

Latin name: *Cercis canadensis*.

BACKGROUND OF THE INVENTION

The present invention relates to a new and distinct variety of *Cercis canadensis*, an Eastern Redbud tree, referred to by its varietal name 'JN2'.

Discovery

I discovered my new tree in the spring, 2006, growing in a production area of a bare-root liner field in Belvidere, Franklin County, Tenn., among a group of cultivated Eastern Redbud trees. The trees were grown from collected seeds planted in 2004.

Propagation

'JN2' was asexually propagated, initially by chip budding onto seedling rootstock, at my direction in the Summer, 2007 at my nursery in Belvidere, Tenn. This propagation and resulting progeny have proven the characteristics of my new variety to be firmly fixed. Furthermore, these observations have confirmed that my new variety represents a new and improved variety of Eastern Redbud tree as particularly evidenced by a golden orange new growth that does not burn, speckled lime green mature foliage, improved vigor in heat and drought, and which can be reliably asexually propagated.

Uniqueness

'JN2' was observed to have a golden orange new growth that does not burn, speckled lime green mature foliage, and improved vigor in heat and drought. These characteristics distinguish my new tree from other typical seedling Eastern Redbud trees and known cultivars. Since my tree is from a seedling of unknown parentage, I cannot compare or contrast the characteristics of my new tree with its parent.

Use

'JN2' was observed for a period of time and is believed to be particularly useful anywhere that Eastern Redbud trees are used; for example, as a specimen tree, or in groupings for a lawn or shrub border, and in naturalized settings. An Eastern Redbud tree with durable, golden orange new growth and speckled lime green foliage is very useful in both residential and commercial landscapes. A heat and drought tolerant selection of Eastern Rosebud trees would be useful in both landscaping and in the nursery.

BRIEF SUMMARY OF THE INVENTION

An Eastern Redbud tree is typically a small, spring-flowering tree with spreading branches forming a rounded canopy of dark green leaves. My new cultivar differs from the species in that it has a golden orange new growth that does not burn, speckled lime green mature foliage, and improved vigor in heat and drought. Eastern Redbud trees are native from northern Florida to New Jersey, and west to Missouri and Texas, and northern Mexico. Eastern Redbud trees prefer moist, well drained soils with a slightly alkaline pH, and grow better in sun than in shade. The tree tolerates a variety of climates ranging from wet to dry, and a variety of soils ranging from alkaline to acidic. The Eastern Redbud tree is considered an understory tree and is very tolerant of competition and nutrient deficiency. It is intolerant of anaerobic soil conditions and will not grow on flooded sites. My new tree has not been observed under all growing conditions, but in a nursery setting in Tennessee, it has been a vigorous grower, and I expect it to perform similarly to the species.

Industry Representation

A cultivated Eastern Redbud tree is represented in the industry by seedling material and several cultivars. Most redbud trees are grown from seed, but there are a number of popular and available cultivars which are propagated by budding or tissue culture. In his Manual of Woody Landscape Plants, Dr. Michael A. Dirr lists 12 cultivars of *Cercis canadensis*, 2 subspecies, and 2 cultivars of the subspecies *texensis*. Although this list is not exhaustive, it does represent what was generally available to the industry prior to 1998. None of these cultivars has the golden orange foliage color of my new tree. A search of the United States Patent and Trademark Office published patents shows 6 patented cultivars, 4 of which do not appear on Dr. Dirr's list. Only one of these, *Cercis canadensis* 'Hearts of Gold' U.S. Plant Pat. No. 17,740 (referred to hereinafter as 'Hearts of Gold') has yellow foliage color. Although there are no industry data on redbud sales, the most popular cultivar of *Cercis canadensis* at the current time is probably *Cercis canadensis* 'Forest Pansy' U.S. Plant Pat. No. 2,556 (hereinafter referred to as 'Forest Pansy'), which has a purple leaf. 'Hearts of Gold' has only been available to the industry for a couple of years, but it is gaining in popularity. It is described in U.S. Plant Pat. No. 17,740 as having "orange-red" new growth, "bright, yellow-green leaves," and "bright golden foliage". My new tree has golden orange new growth and speckled lime-green mature leaves. In the summer of 2007, a severe drought in our area provided an opportunity to observe the durability of these two cultivars side-by-side. 'The Hearts of Gold' redbud tree quit flourishing in late summer and the foliage faded to a pale yellow green and burned in the heat and drought. My 'JN2' redbud tree continued to flourish through the summer, producing new golden orange foliage that did not burn. A late freeze in the spring of 2007 killed back many of the propagules of 'JN2', as well as other seedling and cultivars, and so the largest specimen of my 'JN2' redbud tree, which is two years old, is currently about 4' tall and ¼ in caliper.

BRIEF DESCRIPTION OF THE SEVERAL VIEWS OF THE DRAWINGS

The accompanying photographs depict the color of the tree and foliage of my new variety as nearly as is reasonably possible to make the same in a color illustration of this character.

DESCRIPTION OF THE PREFERRED EMBODIMENT

The following is a detailed description of my new variety of eastern Redbud with color terminology in accordance with The Royal Horticulture Society Colour Chart (R.H.S.), 2005 edition, except where the context indicates a term having its ordinary dictionary meaning. My new tree has not been observed under all growing conditions and variations may occur as a result of different growing conditions. All progeny of my new variety of redbud tree, insofar as have been observed, have been identical in all the characteristics described below.

Other than as set forth below, as of this time, no other characteristics of my new 'JN2' redbud tree have been observed by the inventor which are different from the characteristics common to Eastern Redbud trees.

Parentage: Seedling of unknown parentage grown from collected seed planted in 2004. The parent tree was an Eastern Redbud tree of unknown variety.

Locality where grown and observed: A production field in Belvidere, Franklin County, Tenn.

Figure 1:
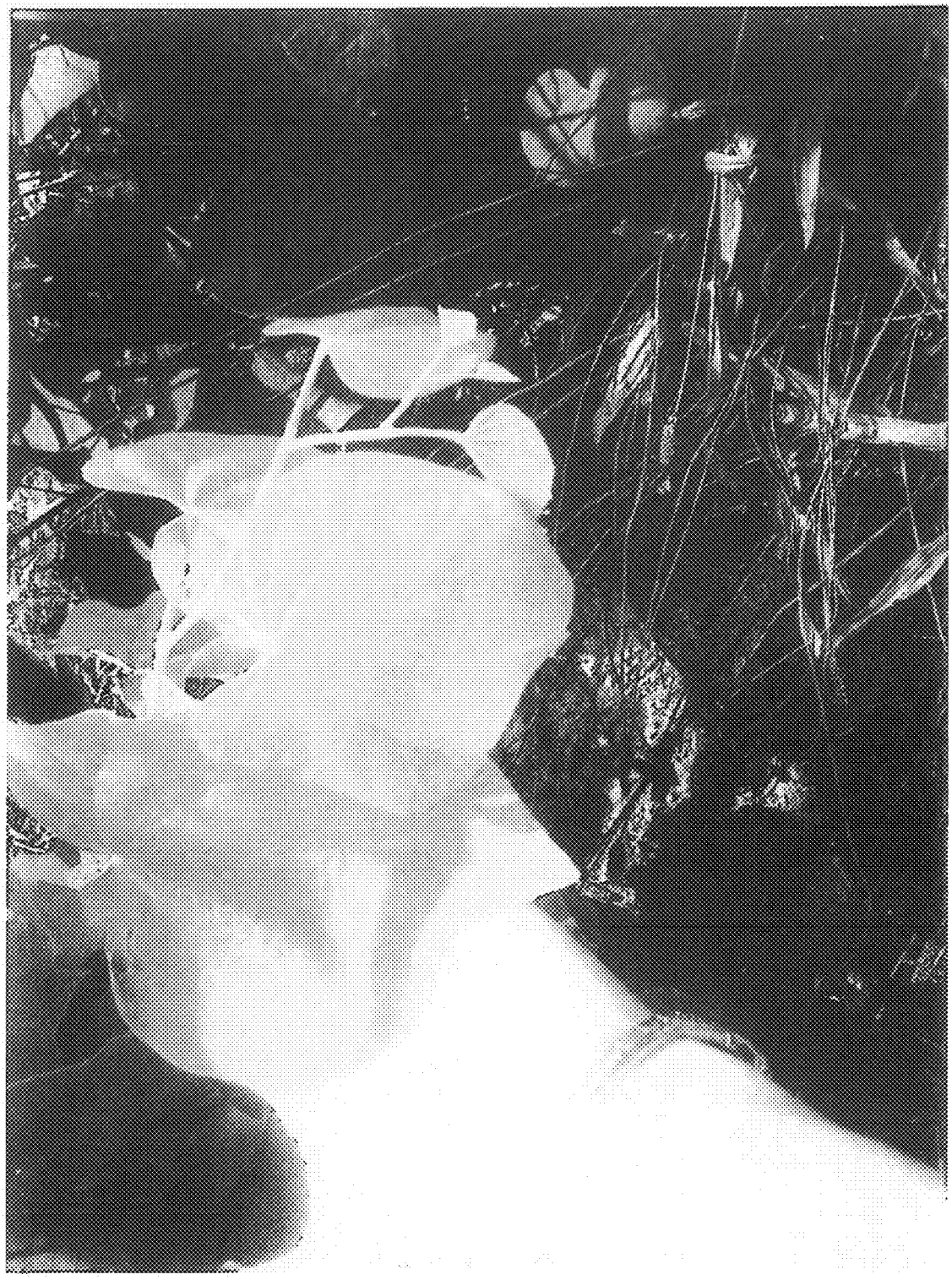
FIG. 1 depicts the development of the new growth of my 'JN2' redbud tree. The newest growth is golden orange (RHS 23B), developing into bright yellow (RHS 6C), then into yellow green (RHS 151D).
Figure 2:
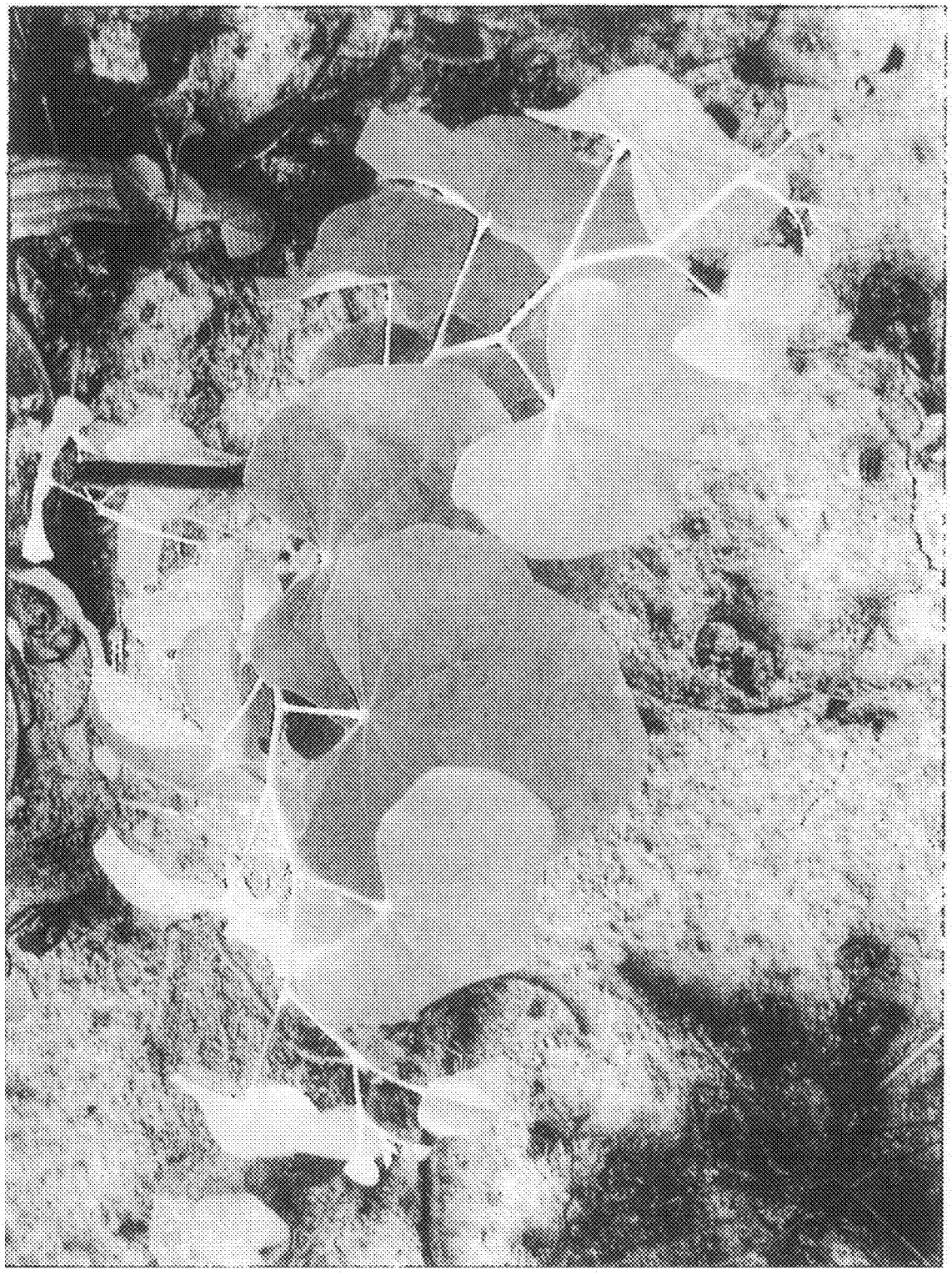
FIG. 2 depicts the full development of foliage from new to mature. The newest growth is golden orange (RHS 23B), developing into bright yellow (RHS 6C), then into yellow green (RHS 151D), finally maturing into light green (RHS 139B) with some lighter and darker speckling.
Figure 3:
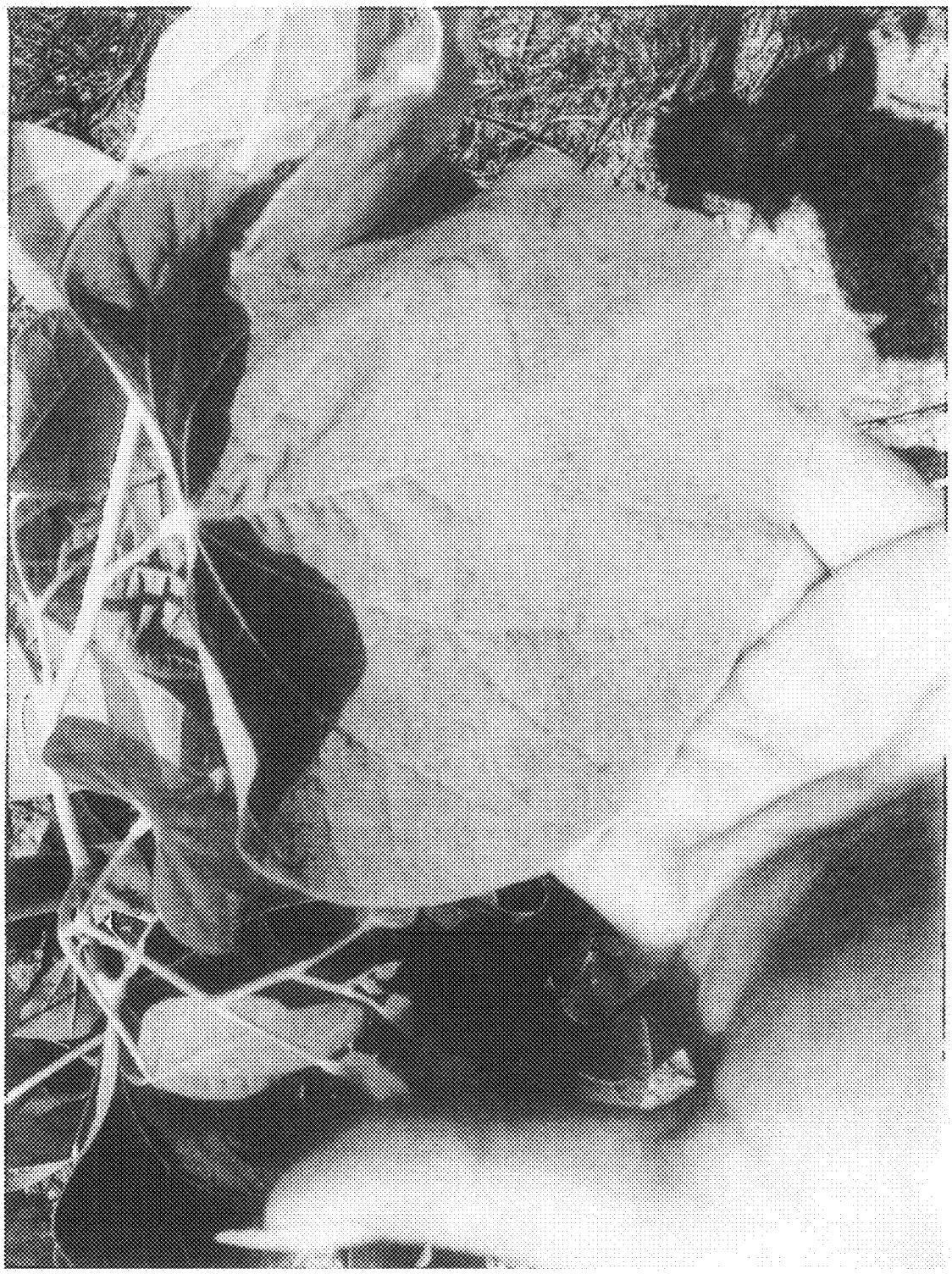
FIG. 3 depicts the speckling which appears as the leaf matures and is best represented as green (RHS 141B) on a yellow green (RHS 153A) background.

Leaves: Slightly larger than is typical of the species, but insignificantly so; opposite, simple, broad-ovate to suborbicular, cordate, acute, entire, 4" to 6" wide by 4" to 6" long. The leaf color develops from a golden orange to a speckled lime green as shown in FIGS. 1 and 2. The new growth is golden orange (RHS 23B), developing into bright yellow (RHS 6C), then into yellow green (RHS 151D). The speckling appears as the leaf matures, as shown in FIG. 3 and is the best represented as green (RHS 141B) on a yellow green (RHS 153A) background. At maturity, as shown by the lower leaves shown in FIG. 2, the leaves are light green (RHS 139B) with some lighter and darker speckling. As show in FIG. 7, fall color is typical of the species, light yellow. The venation pattern consists of a series of primary veins radiating from the base of a leaf toward the apex or outer margin of the leaf. Secondary veins branch off from each side of a primary vein at spaced intervals along the length of the primary vein. The color of the primary veins is a purple pink (RHS 68A).

Petiole: 1½ to 2½ long, emerging orange (RHS 53D) to pink (RHS 50B) and maturing to light green (RHS 153D). FIGS. 1, 2, and 3 show this trait.

Buds: Typical of the species; small laterals ⅛ or less long, blunt, blackish red, somewhat flattened and oppressed, overlapping bud scales, somewhat hairy on the edges. Flower buds are larger (¼) and more rounded than leaf buds and are often clustered around each node.

Figure 5:
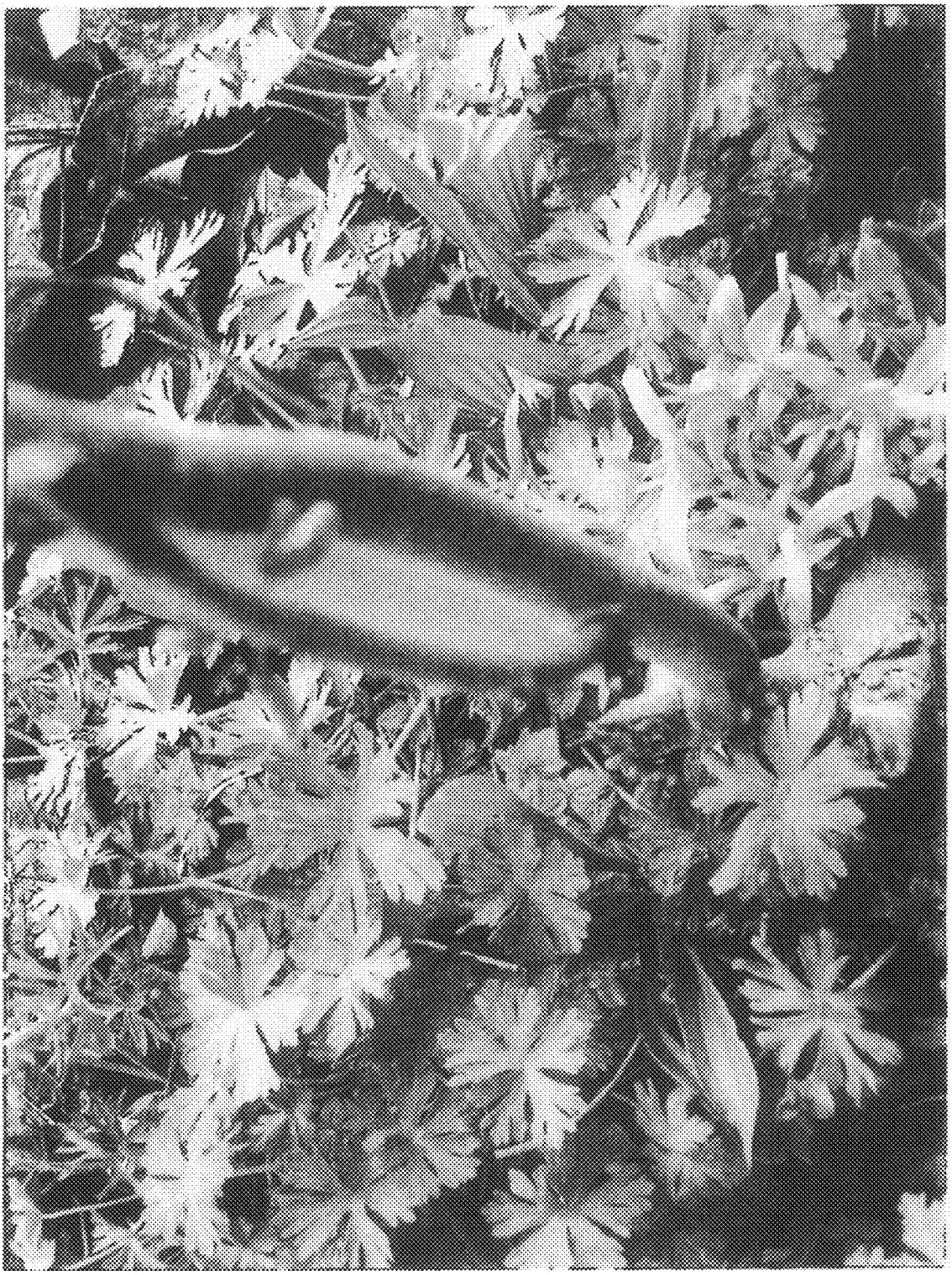
FIG. 5 depicts the flowers of my new tree.
Figure 6:
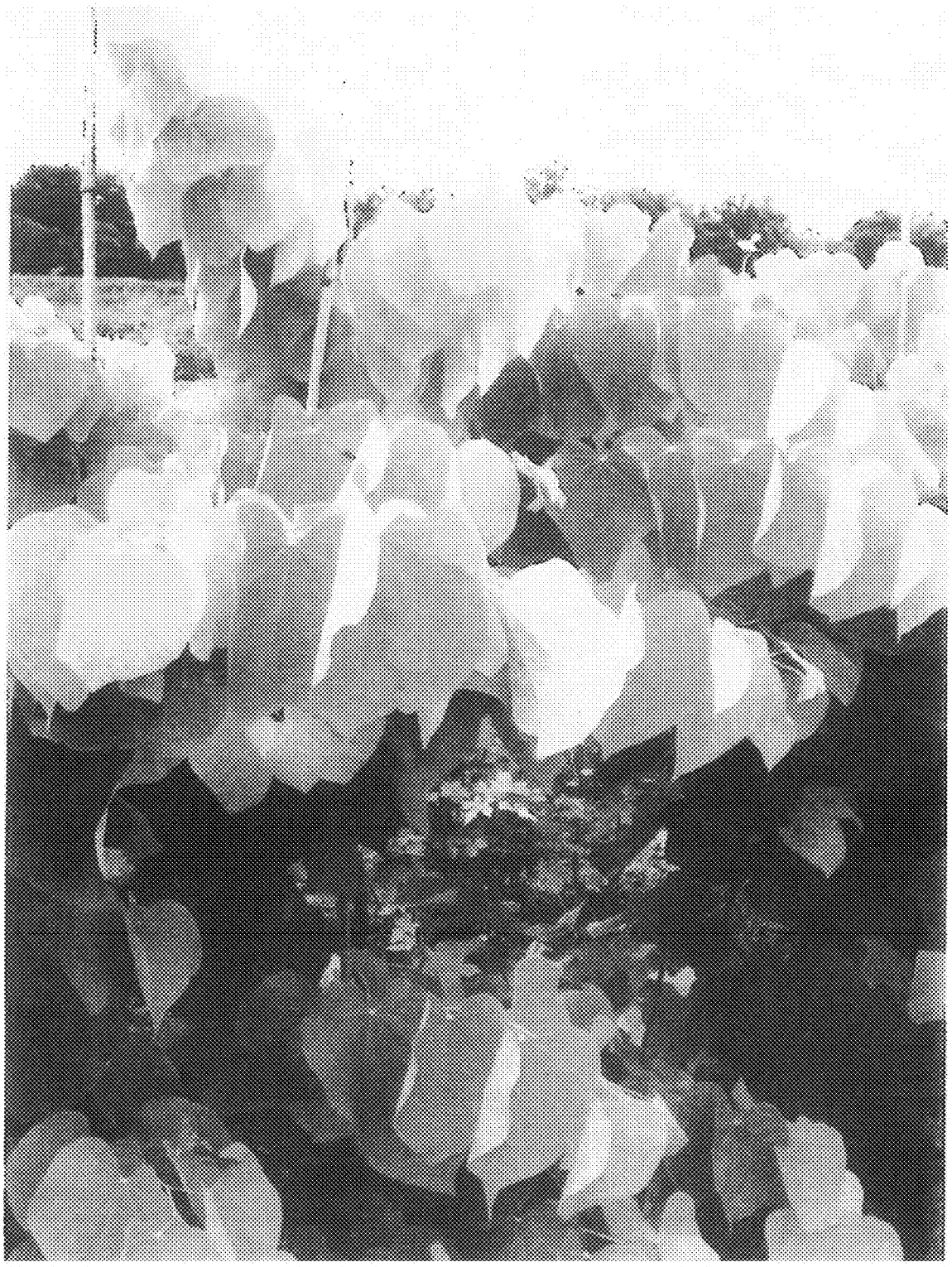
FIG. 6 depicts the fall foliage on my new tree.
Figure 7:
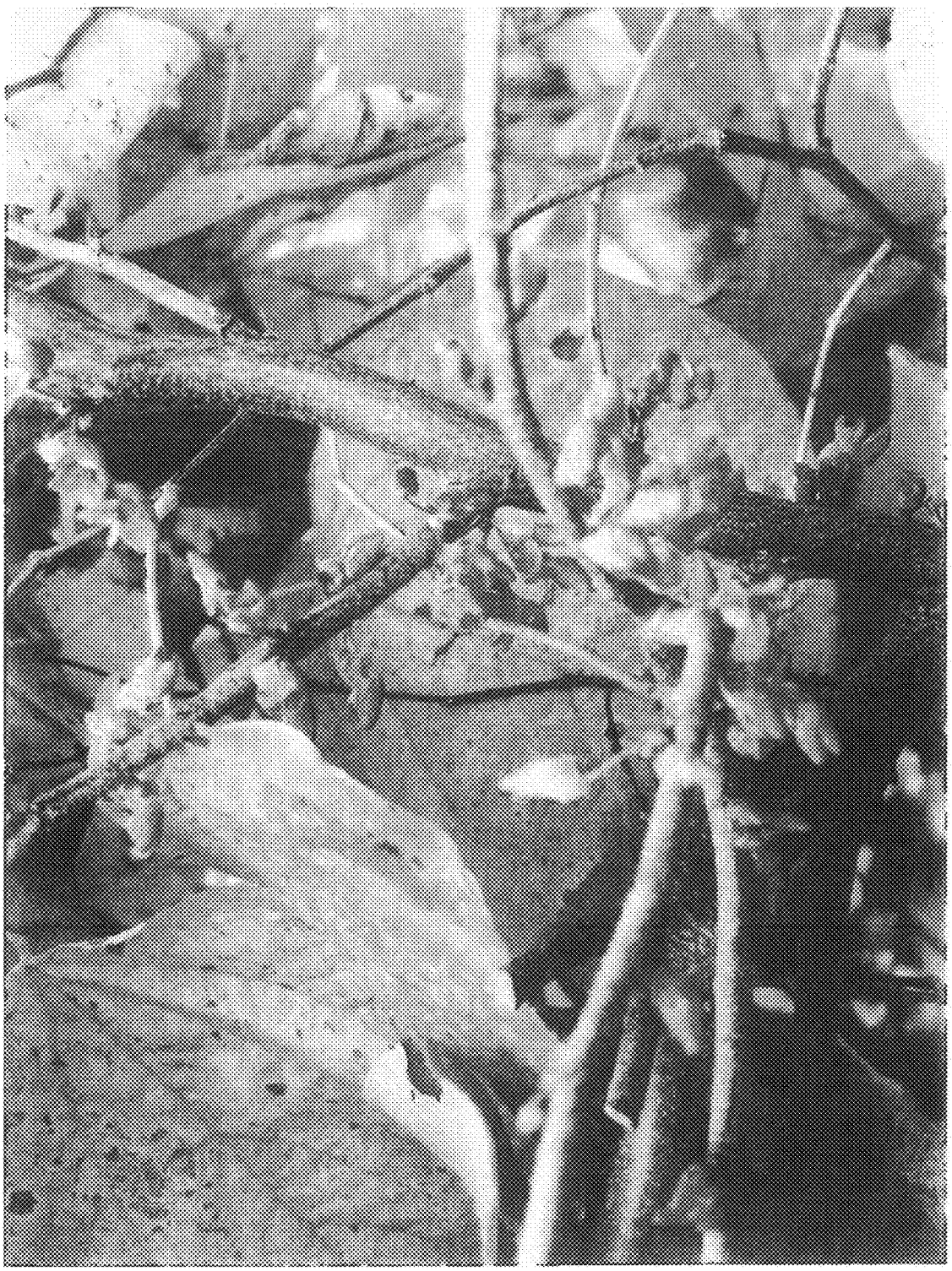
FIG. 7 depicts the branching of my new tree and flowers on my new tree.

Flowers: Typical of the species; perfect, reddish-purple (RHS 63A) in bud opening to a pinkish-purple bloom (RHS 66C); ½ long on a ½ pedicel; flower in March-April for 2-3 weeks; racemose, borne 4"-8" together, often flowering on old trunks 4"-8" in diameter. The species typically flowers in 4-6 years from a seed. My new tree has already flowered after 3 years of observation, as shown in FIGS. 5 and 7.

Fruit: To date, I have observed no fruit on my new tree.

Stem: Slender, glabrous, similar to the petioles in color: initially light yellow (RHS 11A), maturing to light green (RHS 153D) in the first year and then brown in the second year. FIGS. 1, 2, and 3 show this trait.

Trunk: Lighter in color than the species, but not significantly so. The species has a bark that matures to brownish-black (RHS 200A) and develops a scaly condition. My new 'JN2' redbud tree currently has a golden brown mature bark, and although my tree has not been observed for long enough to exhibit this scaly trait, I expect it will be typical of the species.

Figure 4:
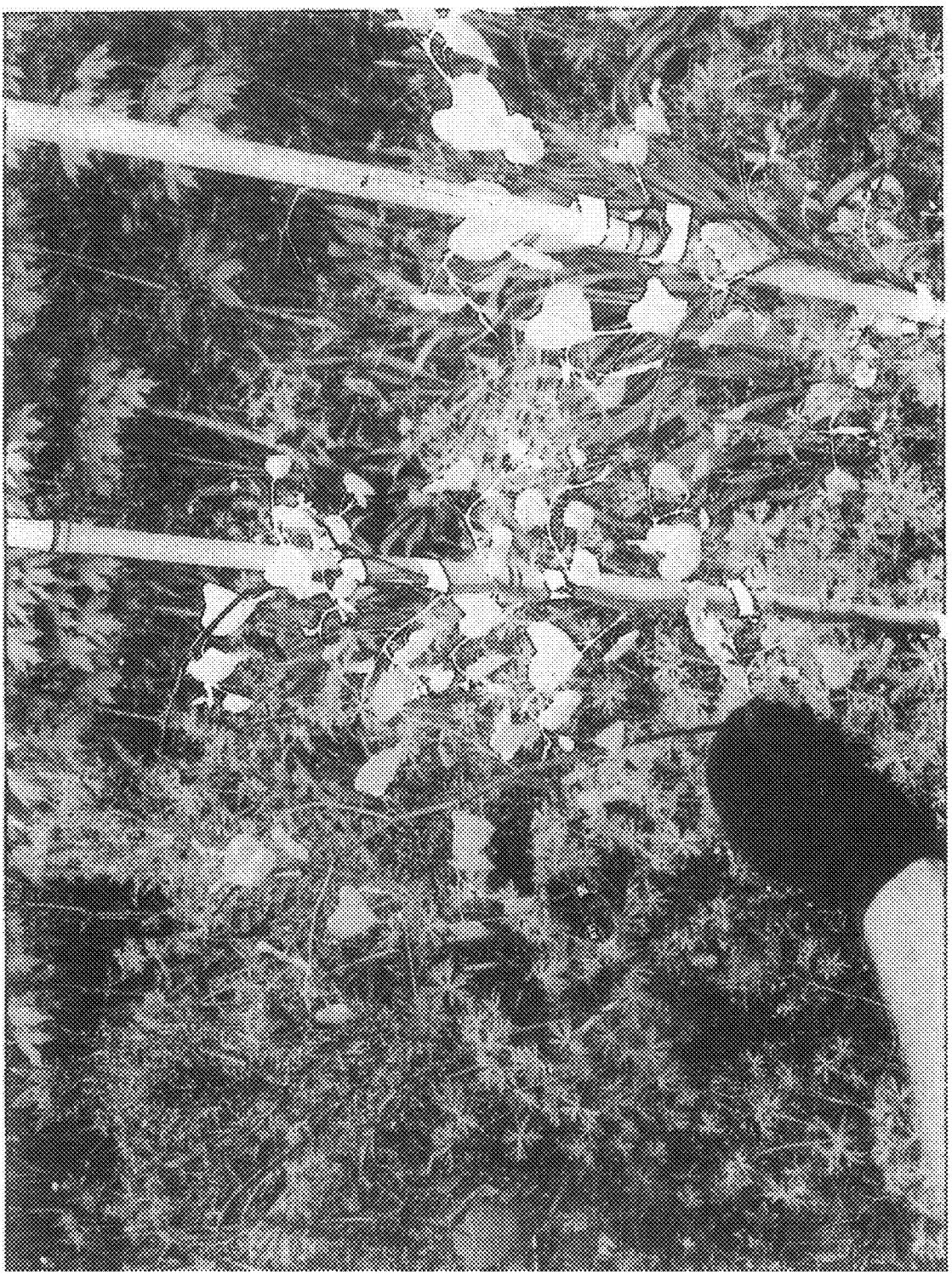
FIG. 4 depicts a comparison between my 'JN2' redbud tree (the two trees on the right) and a cutting of 'Hearts of Gold' on the left. The slightly pendulous habit can be seen on the new growth of my 'JN2' redbud tree in contrast to the less pendulous growth of the 'Hearts of Gold' redbud tree. This figure also shows the contrast of the "orange red" new growth of the 'Hearts of Gold' tree and the golden orange new growth of my new tree.

Branching: Typical of the species with ascending, spreading branches. Both the new growth and mature stems are somewhat pendulous compared to the 'Hearts of Gold' redbud tree, which is described as having "upright stems and primary branches." This trait and comparison between the trees is shown in FIG. 4. As shown in FIG. 7 branches radiate from the trunk of my tree 'JN2' at an acute angel of approximately 45°.

Root system: Redbuds are difficult to propagate from cuttings and all of the propagules of my new 'JN2' redbud tree have been reproduced from chip budding onto seedling rootstocks. The root system of my tree is fibrous and coarse which is typical of the species.

Growth habit: Typical of the species; small, spreading tree with moderate growth rate.

Vigor: More vigorous than the species; performs well in heat and drought;

Diseases: The species is susceptible to canker, verticillium wilt, and leaf spot. I have not observed any of these on my new tree or its propagules.

Pests: Treehoppers, leafhoppers, caterpillars, and scales can all cause damage, but the damage is cosmetic and rare. Redbud as a species is resilient to pests. I have observed no pest problems on my new tree or its propagules.

The invention claimed is:

1. What is claimed is a new and distinct variety of eastern redbud tree named 'JN2' substantially as herein shown and described, characterized particularly as to novelty by a golden orange new growth that does not burn, speckled lime green mature foliage, and improved vigor in heat and drought.

* * * * *